(12) United States Patent
Lee et al.

(10) Patent No.: US 9,192,642 B1
(45) Date of Patent: Nov. 24, 2015

(54) METHOD FOR REDUCING LIVER AND KIDNEY DAMAGE CAUSED BY RADIOTHERAPY

(71) Applicant: Chen-Yu Lee, Taipei (TW)

(72) Inventors: Chen-Yu Lee, Taipei (TW); Da-Tong Ju, Taipei (TW); Hsing-Lung Chao, Taipei (TW); Shih-Fang Chung, Taipei (TW); Hsin-I Ma, New Taipei (TW); Yee-Min Jen, Taipei (TW)

(73) Assignee: Chen-Yu Lee, Taipei (TW)

( * ) Notice: Subject to any disclaimer, the term of this patent is extended or adjusted under 35 U.S.C. 154(b) by 51 days.

(21) Appl. No.: 14/281,976

(22) Filed: May 20, 2014

(51) Int. Cl.
| | |
|---|---|
| *A01N 65/00* | (2009.01) |
| *A61K 36/8888* | (2006.01) |
| *A61K 36/233* | (2006.01) |
| *A61K 36/539* | (2006.01) |
| *A61K 36/65* | (2006.01) |
| *A61K 36/708* | (2006.01) |
| *A61K 36/752* | (2006.01) |
| *A61K 36/725* | (2006.01) |
| *A61K 36/06* | (2006.01) |
| *A61K 36/884* | (2006.01) |
| *A61K 36/284* | (2006.01) |
| *A61K 36/13* | (2006.01) |
| *A61K 36/537* | (2006.01) |
| *A61K 36/236* | (2006.01) |
| *A61K 36/8988* | (2006.01) |
| *A61K 36/258* | (2006.01) |
| *A61K 36/00* | (2006.01) |

(52) U.S. Cl.
CPC ............. *A61K 36/8888* (2013.01); *A61K 36/00* (2013.01); *A61K 36/06* (2013.01); *A61K 36/13* (2013.01); *A61K 36/233* (2013.01); *A61K 36/236* (2013.01); *A61K 36/258* (2013.01); *A61K 36/284* (2013.01); *A61K 36/537* (2013.01); *A61K 36/539* (2013.01); *A61K 36/65* (2013.01); *A61K 36/708* (2013.01); *A61K 36/725* (2013.01); *A61K 36/752* (2013.01); *A61K 36/884* (2013.01); *A61K 36/8988* (2013.01)

(58) Field of Classification Search
CPC ....................................................... A61K 36/00
USPC ......................................................... 424/725
See application file for complete search history.

(56) References Cited

PUBLICATIONS

Chung, Shih-Fang, Study on the effect of clinical formula "Adjusted Da Chai Ling Tang" on cerebral edema and combined syndrome following radiotherapy for intracranial tumors, Dissertation, Liaoning University of Chinese Medicine, Jun. 2013, pp. 1-55.

*Primary Examiner* — Michael Meller
(74) *Attorney, Agent, or Firm* — Bacon & Thomas, PLLC

(57) ABSTRACT

A method for reducing liver and kidney damage caused by radiotherapy is disclosed. The method comprises administering a herbal medicinal composition to a subject in need, wherein the herbal medicinal composition comprises 1.3-5.3 parts by weight of Chaihu, 2.2-8.8 parts by weight of Hunagqing, 1.8-7.0 parts by weight of Panxia, 1.8-7.0 parts by weight of Chishaoyao, 0.5-1.8 parts by weight of Dahuang, 1.3-5.3 parts by weight of Zhishi, 2.2-8.8 parts by weight of Hungtsao, 4.4-17.5 parts by weight of Fuling, 1.8-7.0 parts by weight of Chuling, 2.2-8.8 parts by weight of Zerxie, 1.8-7.0 parts by weight of Changchu, 1.3-5.3 parts by weight of Mahuang, 1.8-7.0 parts by weight of Dansheng, 2.2-8.8 parts by weight of Chuanxiong, 2.2-8.8 parts by weight of Wuchuyu, 2.2-8.8 parts by weight of Tienma, 1.3-5.3 parts by weight of *Ginseng*, and 1.3-5.3 parts by weight of Chuanchi.

1 Claim, No Drawings

METHOD FOR REDUCING LIVER AND KIDNEY DAMAGE CAUSED BY RADIOTHERAPY

BACKGROUND OF THE INVENTION

1. Field of the Invention

The present invention relates to a method for protecting liver and kidney by using an herbal medicinal composition. More particularly, the present invention relates to a method for reducing liver and kidney damage caused by radiotherapy.

2. Description of Related Art

Now, tumor-treatment is often held through Western medicine, comprising: surgery, chemotherapy, and radiotherapy. Radiotherapy combined with chemotherapy is usually conducted as a treating manner, in which mannitol or glycerol is used as the most common dehydrant agent. However, those dehydrant agent may change oxygen, $H_2O$, and electrolyte contents in blood, and consequently increase side effects such as heart and kidney burden. Generally, for patients having the tumor size over 5 cm or severe symptoms like squeezing optic and auricular nerve, surgery combined with radiotherapy and chemotherapy are major treating manners.

Nevertheless, during radiotherapy, radiation passes through tumor as well as normal tissue, directly or indirectly damages liver and kidney tissue and further destroys liver and kidney functions, resulting in liver and kidney damage. Hence, patients suffer from terrible pain caused by liver and kidney damage. Therefore, it is necessary to find safe and efficacious medicines or methods for treating complication caused by radiotherapy.

SUMMARY OF THE INVENTION

The object of the present invention is to provide a method for reducing liver and kidney damage caused by radiotherapy using an herbal medicinal composition. The method can be used to protect liver and kidney tissue from direct or indirect damages after radiation. Therefore, the method of the present invention can relieve the pains caused by radiotherapy to improve the life quality of patients suffering cancer, and assist the efficacy of cancer treatment.

To achieve the object, an aspect of the present invention provides a method for reducing liver and kidney damage caused by radiotherapy, comprising the following steps: administering a herbal medicinal composition to a subject in need; wherein the herbal medicinal composition comprises: 1.3-5.3 parts by weight of Chai Hu (*Bupleurum chinense* DC.), 2.2-8.8 parts by weight of Hunag qing (*Scutellaria baicalensis* Georgi.), 1.8-7.0 parts by weight of Pan Xia (*Pinellia ternate* (Thunb.) Breit.), 1.8-7.0 parts by weight of Chi Shaoyao (*Paeonia veitchii* Lynch), 0.5-1.8 parts by weight of Da Huang (Radix et *Rhizoma Rhei*), 1.3-5.3 parts by weight of Zhishi (*Citrus aurantium* L.), 2.2-8.8 parts by weight of Hung tsao (*Zizyphi Jujubae, Fructus* (red date, red jujubes)), 4.4-17.5 parts by weight of Fuling (*Poria cocos* (Schw.) Wolf.), 1.8-7.0 parts by weight of Chu Ling (*Grifola umbellata* (Pers.) Pilat.), 2.2-8.8 parts by weight of Zer Xie (*Alisma plantago-aquatica* L.), 1.8-7.0 parts by weight of Chang Chu (*Atractylodes lances* (Thunb.) DC.), 1.3-5.3 parts by weight of Ma Huang (*Ephedra sinica* Stapf.), 1.8-7.0 parts by weight of Dan Sheng (*Salvia miltiorrhiza* Bge), 2.2-8.8 parts by weight of Chuanxiong (*Ligusticum chuanxiong* Hort.), 2.2-8.8 parts by weight of Wu Chu Yu (*Evodia rutaecarpa* Benth.), 2.2-8.8 parts by weight of Tien Ma (*Gastrodia elata* Blume), 1.3-5.3 parts by weight of Ginseng (*Panax Ginseng*), and 1.3-5.3 parts by weight of Chuan Chi (*Panax notoginseng* (Burk.) F. H. Chen).

The herbal medicinal composition can be prepared by a method comprising the following steps: mixing 1.3-5.3 parts by weight of Chai Hu, 2.2-8.8 parts by weight of Hunag qing, 1.8-7.0 parts by weight of Pan Xia, 1.8-7.0 parts by weight of Chi Shaoyao, 0.5-1.8 parts by weight of Da Huang, 1.3-5.3 parts by weight of Zhishi, 2.2-8.8 parts by weight of Hung tsao, 4.4-17.5 parts by weight of Fuling, 1.8-7.0 parts by weight of Chu Ling, 2.2-8.8 parts by weight of Zer Xie, 1.8-7.0 parts by weight of Chang Chu, 1.3-5.3 parts by weight of Ma Huang, 1.8-7.0 parts by weight of Dan Sheng, 2.2-8.8 parts by weight of Chuanxiong, 2.2-8.8 parts by weight of Wu Chu Yu, 2.2-8.8 parts by weight of Tien Ma, 1.3-5.3 parts by weight of *Ginseng*, and 1.3-5.3 parts by weight of Chuan Chi to form a mixture; and extracting the mixture with water under heating. However, the herbal medicinal composition is not limited thereto.

Furthermore, in the aforementioned herbal medicinal composition, the Chai Hu is preferably in an amount of 2.0-4.0 parts by weight, the Hunag qing is preferably in an amount of 3.3-6.6 parts by weight, the Pan Xia is preferably in an amount of 2.6-5.3 parts by weight, the Chi Shaoyao is preferably in an amount of 2.6-5.3 parts by weight, the Da Huang is preferably in an amount of 0.7-1.4 parts by weight, the Zhishi is preferably in an amount of 2.0-4.0 parts by weight, the Hung tsao is preferably in an amount of 3.3-6.6 parts by weight, the Fuling is preferably in an amount of 6.6-13.2 parts by weight, the Chu Ling is preferably in an amount of 2.6-5.3 parts by weight, the Zer Xie is preferably in an amount of 3.3-6.6 parts by weight, the Chang Chu is preferably in an amount of 2.6-5.3 parts by weight, the Ma Huang is preferably in an amount of 2.0-4.0 parts by weight, the Dan Sheng is preferably in an amount of 2.6-5.3 parts by weight, the Chuanxiong is preferably in an amount of 3.3-6.6 parts by weight, the Wu Chu Yu is preferably in an amount of 3.3-6.6 parts by weight, the Tien Ma is preferably in an amount of 3.3-6.6 parts by weight, the *Ginseng* is preferably in an amount of 2.0-4.0 parts by weight, and the Chuan Chi is preferably in an amount of 2.0-4.0 parts by weight.

According to the requirement for use, the herbal medicinal composition of the present invention may further comprise at least one of a pharmaceutically acceptable carrier, a diluent, or an excipient generally used in the art. For example, the herbal medicinal composition is encapsulated into liposome to facilitate delivery and absorption; the herbal medicinal composition is diluted with aqueous suspension, dispersion or solution to facilitate injection; or the herbal medicinal composition is prepared in a form of a capsule or tablet for storage and carrying. In addition, the herbal medicinal composition of the present invention may also be administered with any conventional drug or additive together, as long as the treatment effect of the herbal medicinal composition of the present invention are not decreased.

The formulation of Chinese medicine composition emphasizes the principle of "Jun-Chen-Zuo-Shi"; in which "Jun" (emperor) refers to the component for treating the main cause of the disease, "Chen" (minister) refers to the component for enhancing the actions of "Jun" or treating accompanying symptoms "Zuo" (adjuvant) refers to the component for reducing or eliminating possible toxic effects of the Jun or Chen herbs but also treating accompanying symptoms, and "Shi" (courier) refers to the component for facilitating the delivery or guide of the other herbs to the target organs. In addition, Chinese medicine is easier transported through brain blood barrier than Western medicine. Briefly, Chinese medicine composition is a prescription, which can combine the properties between drugs to comply with each other. The principle of Chinese medicine is totally different from Western medicine which uses only one drug.

During radiotherapy, radiation passes through tumor as well as normal tissue, directly or indirectly damages liver and kidney tissue and further destroys liver and kidney functions of patients, resulting in liver and kidney damage. The method of the present invention can be used to protect liver and kidney tissue by using an herbal medicinal composition. Therefore, the method of the present invention can relieve the pains caused by radiotherapy to improve the life quality of patients suffering cancer, and assist the efficacy of cancer treatment.

Hepatocytes and renal cells can be protected from necrosis by taking the herbal medicinal composition of the present invention. On the other hand, the damaged liver and kidney tissue, the dysfunction of the liver and kidney, and the abnormal bile secretion (comprising bilirubin, bile salt, and cholesterol secretion) caused by radiation can be recovered by taking the herbal medicinal composition of the present invention.

Other objects, advantages, and novel features of the invention will become more apparent from the following detailed description when taken in conjunction with the accompanying drawings.

DETAILED DESCRIPTION OF THE PREFERRED EMBODIMENT

According to the specific embodiments illustrating the practice of the present invention, a person having ordinary skill in the art can easily understand other advantages and efficiency of the present invention through the content disclosed therein. The present invention can also be practiced or applied by other variant embodiments. Many other possible modifications and variations of any detail in the present specification based on different outlooks and applications can be made without departing from the spirit of the invention.

[Preparation of Herbal Medicinal Composition]

Chai Hu (9 g), Hunag qing (15 g), Pan Xia (12 g), Chi Shaoyao (12 g), Da Huang (3 g), Zhishi (12 g), Hung tsao (15 g), Fuling (30 g), Chu Ling (12 g), Zer Xie (15 g), Chang Chu (12 g), Ma Huang (9 g), Dan Sheng (12 g), Chuanxiong (15 g), Wu Chu Yu (15 g), and Tien Ma (15 g) were cut into slices if necessary, and then heated with water (1200 g) at 90° C. or more for 60 to 90 minutes to form an extract (480 g). Herbal residues were removed and then powders of *Ginseng* (9 g) and Chuan Chi (9 g) were added into the extract. These herbal medicinal materials are selected and decocted under Dr Lee's (Yu Sheng Clinic) supervision. The aforementioned herbal medicinal materials were extracted by automatic medicinal herb decocting device (AMOS DP-200) and the obtained liquid extract was distributed evenly in 3 dosages (160 ml/dosage), which was administered three times a day. Most parts of herbal medicinal materials were produced from Mainland China and imported into Taiwan, and only small parts of medicinal materials were locally produced from Taiwan. All herbal medicinal materials were approved by Committee on Chinese Medicnine and Pharmacy, Departmemt of Health, Executive Yuan.

[Experiment Subjects]

Volunteers were collected from Hematology Oncology and Neurological Surgery Departments of Tri-Service General Hospital (Taiwan) during the period of July, 2011 until May, 2013. The volunteers comprise the patients having primary brain tumor or recurrence thereof after surgery, or metastatic brain tumor from other organism such as lung cancer, lymphatic cancer, and breast cancer; or the one needed radiotherapy after surgery. All volunteers has already suffered cerebral edema and evaluated to do radiotherapy. During radiotherapy, the herbal medicinal composition was administered to the volunteers 3 dosages per day for 10 days and they are arranged to do MRI and serum analysis. Their clinical symptoms were also observed and recorded.

Before separating into 2 groups, all patients were arranged to conduct serum analysis on liver and kidney functions, and on MRI of cerebral edema. The appropriate patients were selected and separated randomly, and classified into two groups named "Treatment Group" and "Control Group" respectively comprising 22 patients. "Treatment Group" received radiotherapy along with the herbal medicinal composition of the present invention, and "Control Group" solely received radiotherapy without taking the herbal medicinal composition of the present invention. "Treatment Group" includes 10 men and 12 women, 40 to 77 years old, average 56±0.4 years old, and 1.76±0.12 years course. "Control Group" includes 14 men and 10 women, 20 to 82 years old, average 57±0.88 years old, and 1.80±0.11 years course. Sex, age, course, and condition between 2 groups represented without significant difference ($p>0.05$).

[Experiment Method]

Treatment Group: The patients were conducted routine treating process based on Western medicine, and further took the herbal medicinal composition of the present invention with 3 dosages per day for total 10 days.

Control group: The patients were only conducted routine treating process based on Western medicine.

Those patients were tracked on 4th, 7th, 10th and 14th days after the treatment started to record their physical status. In order to take the baseline data, they were also arranged to receive MRI and serum analysis on glutamate oxaloacetate transaminase (GOT), glutamate pyruvate transaminase (GPT), T-bilirubin, blood urea nitrogen (BUN) and Creatinine. Blood hemogram of the mentioned markers are reliable for observation on radiotherapy.

Serum glutamic oxaloacetic transaminase (GOT) is a marker for evaluating liver and heart functions and myopathies. On clinical experience, GOT value is escalated along with cranial nerves dissolved gradually or infected with acute toxic hepatitis. Serum glutamate pyruvate transaminase (GPT) is an important marker for evaluating damage in hepatocytes as well as evaluating treatment efficacy of liver diseases. The higher GPT value represents the more serious level of inflammation or damage existed in hepatocytes. T-bilirubin is a marker for evaluating hepatobiliary disease and hemolytic disease. Serum blood urea nitrogen (BUN) is a casual marker for evaluating kidney function applied on kidney diseases, for example, renal insufficiency, acute or chronic glomerulonephritis, annephrotic syndrome and so on. Creatinine is a marker for evaluating glomerular filtration rate (GFR) and usually applied for monitoring kidney function. On clinical experience, all of GPT Serum, T-bilirubin, BUN, and creatinine values are increased while cerebral edema or cranial nerves damage.

The complications of radiotherapy on cerebral edema include headache, dizziness, spasm, nausea, vomit and fatigue. The Chinese medical methodology as for examining above symptoms is visual analogue scale (VAS), as shown in Table 1. Grades for treatment efficacy=[(Total integration after treatment)/(Total integration before treatment)]×100%.

TABLE 1

| Symptom | None (0 degree) | Mild (1 to 3 degree) | Moderate (4 to 6 degrees) | Severe (7 to 10 degrees) |
|---|---|---|---|---|
| Headache | None | Sometimes happened, and auto-released in 1 hr or released after excretion. | Often happened and can be tolerated, and auto-released in 1-3 hr. | Heavy headache and cannot be tolerated, continued >3 hr and released after taking medicine. |
| Dizziness | None | Sometimes happened, and auto-released in 1 hr. | Often happened, and auto-released in 1-3 hr. | Always happened, continued >3 hr and released after taking medicine. |
| Spasm | None | Increased within 1 time compared with before treatment. | Increased 2-3 times compared with before treatment. | Increased more than 3 times compared with before treatment. |
| Vomit | None | Nausea happened less than 2 times per day without vomit. | Nausea happened about 3-4 times per day with foaming at mouth or vomiting food residues. | Nausea happened obviously and accompanied with vomiting food residues more than 4 times per day. |
| Fatigue | None | Sometimes happened, and auto-released in 1 hr. | Often happened, and auto-released in 1-3 hr. | Obviously happened every day, continued >3 hr |

[Statistical Analysis]

For each set of values, data were expressed as the means±standard deviation (SD). Three independent experiments were performed and non-categorical variables were compared using the Student's t-test. All P-values were two-tailed, with values of $P<0.05$ considered significant.

[Results]

Visual analogue scale (VAS)

Since intracranial tumor expanded from infiltrating growth thereof, cerebral edema must be formed while a certain area is occupied by tumor. Accordingly, the intracranial pressure raised and further oppressed brain tissue and artery, leading to central nerve damage. Cerebral edema is easily formed or getting worse after radiotherapy. Meanwhile, complications are shown by chemotherapy, for example, headache, dizziness, nausea, cramps, fatigue, skin inflammation and infection, hair loss and so on. With regard to those complications, we observed symptoms variation compared between "Treatment Group" and "Control Group" based on Visual analogue scale (VAS) after radiotherapy. "Treatment Group" took medicine when radiotherapy started. Those patients of two groups were tracked on 4th, 7th, 10th and 14th days after the treatment started to record their physical status about headache, dizziness, spasm, vomit, and fatigue and analyzed as well. The results were listed in Table 2.

TABLE 2

| Symptom | Groups | Day 4 | Day 7 | Day 10 |
|---|---|---|---|---|
| Headache | Treatment Group | 0 ± 0 | 0 ± 0 | 0.13 ± 0.14 |
|  | Control Group | 0.25 ± 0.24 | 0.5 ± 0.48 | 1.0 ± 0.96 |
| Dizziness | Treatment Group | 0.25 ± 0.24 | 0.25 ± 0.24 | 0.13 ± 0.14 |
|  | Control Group | 0.13 ± 0.14 | 0.38 ± 0.34 | 1.0 ± 0.96 |
| Spasm | Treatment Group | 0 ± 0 | 0 ± 0 | 0 ± 0 |
|  | Control Group | 0 ± 0 | 0 ± 0 | 0 ± 0 |
| Vomit | Treatment Group | 0.38 ± 0.34 | 0.13 ± 0.14 | 0.25 ± 0.24 |
|  | Control Group | 0.25 ± 0.24 | 0.38 ± 0.34 | 1.5 ± 1.3 |
| Fatigue | Treatment Group | 0.13 ± 0.14 | 0.63 ± 0.6 | 1.13 ± 1.08 |
|  | Control Group | 0.25 ± 0.24 | 1.25 ± 1.2 | 2.25 ± 2.16 |

Cerebral edema is easily formed or getting worse after radiotherapy, and typical type of clinical performance is severe headache. Hence, headache is the first observed item after radiotherapy. Referring to Table 2, difference was observed on Day 4 and significant discrepancy was shown on Day 7 and Day 10 ($p=0.046$ and $0.037$, respectively). Other typical clinical symptoms of cerebral edema include severe dizziness, spasm, vomit, and fatigue, so it also specified in observation list after radiotherapy. With regard to Table 2, difference was observed on Day 7 and significant discrepancy was shown on Day 10 ($p=0.037$) for dizziness; difference was observed was on Day 7 and significant discrepancy was shown on Day 10 ($p=0.001$) for vomit; and difference was observed on Day 4 and significant discrepancy was shown on Day 10 ($p=0.037$) for fatigue.

For the whole status of the patients, the symptoms of "Treatment Group" are milder than "Control Group" and there was significant discrepancy between two groups ($p<0.05$).

Besides, "Treatment Group" reveals higher grades for vomit than "Control Group" on Day 4, which may be attributed to the reason that patients felt uncomfortable in the beginning of taking Chinese medicine. On clinical experience, spasm induced by cerebral edema after radiotherapy was in a ratio of about 1/15. Compared between "Treatment Group" and "Control Group" on spasm issue, no patient having fatigue symptom was observed within 2 groups. It represents that the radiotherapy is conducted on safety dose condition. Above all, the results proved that the herbal medicinal composition of the present invention has efficacy for protecting brain and decreasing cerebral edema, and further improve the life quality of patients.

MRI Analysis

Some patients have already suffered from severed cerebral edema, and even some patients had headache or dizziness caused by cerebral edema and high intracranial pressure or had hand and foot weakness. These patients admitted into hospital via emergency and the cerebral edema thereof was getting worse after radiotherapy. Therefore, the MRI evaluation after radiotherapy was based on the original MRI status. The results were listed in Table 3.

TABLE 3

| Group | MRI indication before radiotherapy | MRI indication after radiotherapy |
|---|---|---|
| Treatment Group | 1.56 ± 1.76 | 0.79 ± 0.70 |
| Control Group | 0.67 ± 0.69 | 0.50 ± 0.48 |

T2W and DWI were applied to compare the MRI scales of cerebral edema before and after treatment. The result proved that the range of cerebral edema in "Treatment Group" was smaller than "Control Group"; and the statistical discrepancy was observed ($p=0.046$, $p<0.05$). Meanwhile, the range of intracranial tumor in "Treatment Group" was smaller than "Control Group"; and the statistical discrepancy was observed ($p=0.049$, $p<0.05$).

Serum Analysis

Liver and kidney functions were examined by serum test before and after treatment. The result showed that hepatotoxicity and renal toxicity were not induced by the herbal medicinal composition of the present invention. The results of two groups were analyzed and listed in Table 4.

TABLE 4

| Item | Treatment Group | | Control Group |
| --- | --- | --- | --- |
| | Ratio before treatment (average ± S.D) | Ratio after treatment (average ± S.D) | Ratio after treatment (average ± S.D) |
| GOT | 0.04 ± 0.48 | 0.25 ± 0.60 | 0.03 ± 0.96 |
| GPT | 0.06 ± 0.62 | 0.29 ± 0.68 | 0.03 ± 0.32 |
| T-bilirubin | 0.13 ± 0.56 | 0.36 ± 0.74 | 0.11 ± 0.20 |
| BUN | 0.20 ± 1.20 | 1.00 ± 0.86 | 0.11 ± 0.21 |
| Creatinine | 0.10 ± 0.32 | 1.10 ± 0.96 | 0.05 ± 0.83 |

Compared the results of "Treatment Group" before and after treatment, the significant discrepancy was shown in GOT ($p=0.0001$, $p<0.05$), GPT ($p=0.0002$, $p<0.05$), and T-bilirubin ($p=0.05$, $p>0.05$). This result represents the significant discrepancy in liver function. On the other hand, the significant discrepancy also shown in Creatinine ($p=0.046$, $p<0.05$), and this result represents the significant discrepancy in kidney function.

Further compared the results of "Treatment Group" and "Control Group" after treatment, "Treatment Group" performed better results than "Control Group" significantly (GOT: $p=0.001$, $p<0.05$; GPT: $p=0.002$, $p<0.05$; T-Bilirubin: $p=0.005$, $p<0.05$; BUN: $p=0.058$, $p>0.05$; and Creatinine: $p=0.046$, $p<0.05$).

According to the mentioned blood hemogram results, it proved that the herb medicinal composition of the present invention exhibit effect to constrain the development of cerebral edema, prevent brain tissue from being hypoxia and weakened blood vessels, decrease brain tissue damage, and abolish the cranial nerves dissolution during radiotherapy process. Meanwhile, the herb medicinal composition of the present invention eliminates the brain tissue of patients from burn injury by the radiation, and thus avoids brain tissue from apoptosis. Hence, the herb medicinal composition of the present invention has protection effect on livers and kidneys.

Radiotherapy is considered as an important manner for tumor treatment. However, liver and kidney damage is a possible side effect during the radiotherapy process. Radiation passes through tumor as well as normal tissue, directly or indirectly damages liver and kidney tissue and further destroys liver and kidney functions. Hence, patients feel terrible pain caused by liver and kidney damage. Therefore, the herb medicinal composition of the present invention recovers the damage liver and kidney tissue of patients caused by the radiation, and thus avoids hepatocytes and renal cells from necrosis. During radiotherapy process, the herb medicinal composition of the present invention exhibits effect to protect liver and kidney from direct or indirect damaged by radiation. On the other hand, the damaged liver and kidney tissue, the dysfunction of the liver and kidney, and the abnormal bile secretion (comprising bilirubin, bile salt, and cholesterol secretion) caused by radiation can be recovered by taking the herbal medicinal composition of the present invention.

Although the present invention has been explained in relation to its preferred embodiment, it is to be understood that many other possible modifications and variations can be made without departing from the spirit and scope of the invention as hereinafter claimed.

What is claimed is:

1. A method for reducing liver and kidney damage from radiotherapy in a human in need thereof consisting essentially of administering to said human a composition consisting essentially of therapeutically effective amounts of an extract of *Bupleurum chinense* DC., an extract of *Scutellaria baicalensis* Georgi., an extract of *Pinellia ternate* (Thunb.) Breit., an extract of *Paeonia veitchii* Lynch, an extract of Radix et *Rhizoma Rhei*, an extract of *Citrus aurantium* L., an extract of *Zizyphi Jujubae, Fructus*, an extract of *Poria cocos* (Schw.) Wolf, an extract of *Grifola umbellata* (Pers.) Pilat., an extract of *Alisma plantago-aquatica* L., an extract of *Atractylodes lances* (Thunb.) DC., an extract of *Ephedra sinica* Stapf., an extract of *Salvia miltiorrhiza* Bge, an extract of *Ligusticum chuanxiong* Hort., an extract of *Evodia rutaecarpa* Benth., an extract of *Gastrodia elata* Blume, an extract of *Panax Ginseng*, and an extract of *Panax notoginseng* (Burk.) F. H. Chen.

* * * * *